(12) United States Patent
Main et al.

(10) Patent No.: US 10,314,407 B1
(45) Date of Patent: Jun. 11, 2019

(54) INTELLIGENT SLEEP ECOSYSTEM

(71) Applicant: XSENSOR Technology Corporation, Calgary (CA)

(72) Inventors: Ian Main, Calgary (CA); Madeleine Breen Townley, Calgary (CA); Curtis Anderson, Calgary (CA); Melissa Elizabeth Remus Jones, Calgary (CA)

(73) Assignee: XSENSOR Technology Corporation, Calgary, Alberta (CA)

( * ) Notice: Subject to any disclaimer, the term of this patent is extended or adjusted under 35 U.S.C. 154(b) by 681 days.

(21) Appl. No.: 14/701,340

(22) Filed: Apr. 30, 2015

Related U.S. Application Data

(60) Provisional application No. 61/986,812, filed on Apr. 30, 2014.

(51) Int. Cl.
*A47C 27/08* (2006.01)
*A47C 27/14* (2006.01)
*A47C 21/04* (2006.01)
*A47C 27/10* (2006.01)
*A47C 21/00* (2006.01)
*A61M 21/02* (2006.01)
*A61B 5/00* (2006.01)
*A61M 21/00* (2006.01)

(52) U.S. Cl.
CPC .......... *A47C 27/082* (2013.01); *A47C 21/003* (2013.01); *A47C 21/046* (2013.01); *A47C 21/048* (2013.01); *A47C 27/10* (2013.01); *A47C 27/146* (2013.01); *A61B 5/4809* (2013.01); *A61B 5/4812* (2013.01); *A61B 5/6892* (2013.01); *A61M 21/02* (2013.01); *A61B 2562/0247* (2013.01); *A61M 2021/0027* (2013.01); *A61M 2021/0044* (2013.01); *A61M 2021/0066* (2013.01); *A61M 2205/3303* (2013.01); *A61M 2205/3306* (2013.01); *A61M 2230/06* (2013.01); *A61M 2230/42* (2013.01); *A61M 2230/62* (2013.01); *A61M 2230/63* (2013.01)

(58) Field of Classification Search
CPC ... A47C 27/061; A47C 27/083; A47C 27/082; A47C 23/0435; A47C 27/064; A47C 31/123
See application file for complete search history.

(56) References Cited

U.S. PATENT DOCUMENTS 9,186,479 B1 * 11/2015 Franceschetti ....... A61B 5/4266
2008/0052837 A1 * 3/2008 Blumberg ............ A47C 23/002
5/727

(Continued)

FOREIGN PATENT DOCUMENTS

WO WO 2012/160502 A1 11/2012
WO WO 2014/145436 A1 9/2014

Primary Examiner — Eric J Kurilla
(74) Attorney, Agent, or Firm — Fenwick & West LLP

(57) ABSTRACT

An improved sleep system includes an actively responsive bed and mattress combination. The system adjusts the contour and microclimate of the mattress surface, in addition to the ambient conditions of the sleep environment based on the user's preferences and physiological state. A variety of technologies are integrated into the sleep system in order to determine the settings for an improved sleep environment, and automatically adjust the mattress firmness, bed surface temperature, humidity, and/or ambient light and sound.

23 Claims, 14 Drawing Sheets

(56) References Cited

U.S. PATENT DOCUMENTS

| | | | |
|---|---|---|---|
| 2010/0317930 A1* | 12/2010 | Oexman | A47C 31/123 600/300 |
| 2012/0296156 A1* | 11/2012 | Auphan | A61M 21/02 600/28 |
| 2012/0311790 A1* | 12/2012 | Nomura | A61G 7/05776 5/710 |
| 2013/0000047 A1* | 1/2013 | McCann | A47C 27/082 5/709 |
| 2013/0283530 A1* | 10/2013 | Main | A47C 31/12 5/600 |

* cited by examiner

| Sleep Stage | | Actions/Settings/Features | | | |
|---|---|---|---|---|---|
| | | Comfort and Support | Environment Control | | |
| | | | Temperature | Light | Sound |
| Occupied 202 | Awake 208 | Default | Default, warm | Set preference, adjust to ambient Evening: warm tone Day time: cool tone | Default |
| | Falling Asleep 206 | Softer, adjust to position | Warm feet cool torso | Dusk simulation: warm tone, slow dimming | Noise screening, relaxing sounds |
| | Asleep | Firmer, adjust to position | Cool | Off | Noise screening, sleep-enhancing sounds |
| | Waking up 204 | Gradually return to default | Cool feet warm torso | Dawn Simulation: cool tone, slow brightening | Alertness-inducing sounds |
| Unoccupied 210 | Bed Exit | Suspend auto-adjust | Default, warm | Warm tone under-bed lights | Off |
| | Empty Bed | Default | Off | Off | Off |

FIG. 3

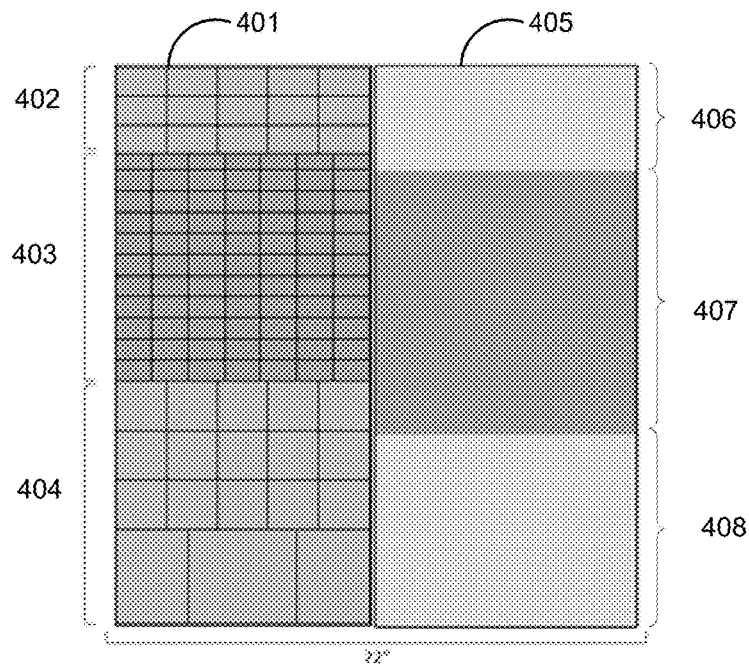

FIG. 4A

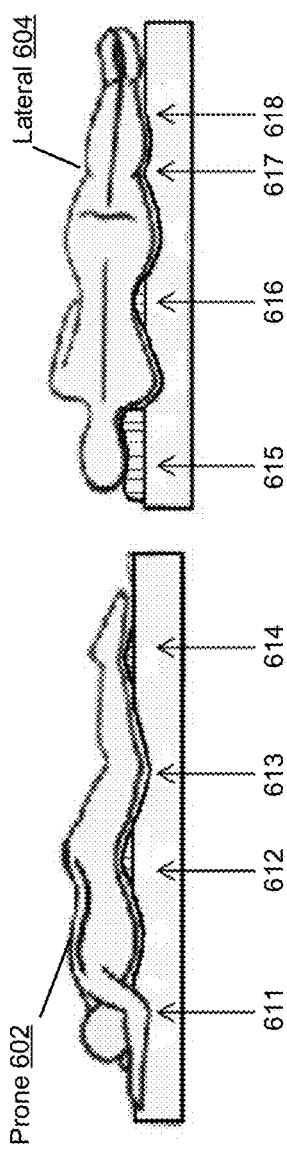

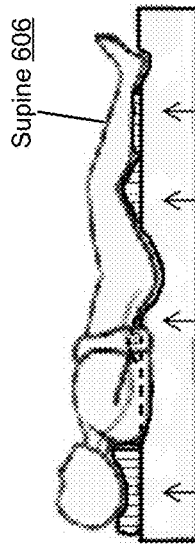

| Position | Prone | Lateral | Supine |
|---|---|---|---|
| Settings | 611: Low head zone support<br>612: Low lumbar spine zone support<br>613: No knee zone support<br>614: Medium calf/ankle zone support | 615: High head zone support<br>616: High lumbar spine zone support<br>617: Low or no knee zone support<br>618: Low or no calf/ankle zone support | 619: Medium/low head zone support<br>620: Medium lumbar spine zone support<br>621: High knee zone support<br>622: Calf/ankle zone support for heel pressure relief |

FIG. 6B

| Name | Description |
|---|---|
| Coverage | Proportion of image covered |
| Per25 | Coverage of 25% of pressure |
| Per50 | Coverage of 50% of pressure |
| Per75 | Coverage of 75% of pressure |
| Reg1 - Reg8 | Coverage over 8 fixed rectangular regions |
| Symmetry | Measure of pressure symmetry |
| Balance | Measure of pressure on both sides of image |
| DirCurve | Measure of curvature of pressure image |

US 10,314,407 B1

INTELLIGENT SLEEP ECOSYSTEM

CROSS-REFERENCE TO RELATED APPLICATION(S)

This application claims priority under 35 U.S.C. § 119(e) to U.S. Provisional Patent Application Ser. No. 61/986,812, "Intelligent Sleep Ecosystem," filed Apr. 30, 2014. The subject matter of the foregoing is incorporated herein by reference in its entirety.

BACKGROUND OF THE INVENTION

1. Field of the Invention

This invention relates generally to sleep systems.

2. Description of the Related Art

Sleep is important. Choosing the right mattress is essential to a restful sleep. People generally alternate between sleeping on their side, back, or stomach, and as a result, it is difficult to choose a mattress that provides the right support and comfort for different sleep positions. Discomfort during sleep disrupts a restful sleep and affects a person's productivity, concentration, and health. There is always a need for better sleep systems.

SUMMARY

One example of an improved sleep system is referred to as the Intelligent Sleep Ecosystem (ISE). It includes an actively responsive sleep support system (e.g., a bed and mattress combination). The system adjusts the contour and microclimate of the sleep surface (e.g., a mattress surface), in addition to the ambient conditions of the sleep environment based on the user's preferences and physiological state. A variety of technologies may be integrated into the ISE in order to determine the settings for an improved sleep environment, for example to automatically adjust the mattress firmness, bed surface temperature, humidity, and/or ambient light and sound.

The ISE can also be customizable to the individual user's needs at each moment during the night, and over time becomes tailored to the user's preferences, habits and body type. Actively adjusting the mattress to the user's body position facilitates a more restorative sleep and fewer aches and pains in the morning. In addition, controlling the bedroom environment helps the user fall asleep faster and wake up easier. Furthermore, the ISE can smooth over night-time disruptions, lulling the user back to sleep, and provide enhanced safety during the night by connecting with emergency alert systems. Lastly, integrating technology into the sleep environment provides convenience and opportunities to connect and coordinate with other devices.

Alternate embodiments include only some of the features described above or elsewhere in this document. For example, one aspect is detecting a person's posture and adjusting the sleep support system according to the person's posture. Another aspect is detecting a person's sleep state and adjusting a sleep environment for the person according to the person's sleep state. A further aspect is controlling the sleep environment through an intelligent state machine. Yet another aspect is, when predicting sleep stage, using machine vision to determine the location of the person's thorax and sampling the area at an increased rate to extract heart and breathing rates using signal processing. Still another aspect is matching sleep stage with a set of environmental conditions designed to provide the best possible sleep. Other aspects include an integrated temperature adjustable system such as an air-conditioning system to provide a "curtain" of air over the sleeper, and a zoned temperature control which reacts to the user's body temperature and sleep state. As a final example, another aspect is a method of adjusting the mattress contour according to the sleeper's position as determined by machine vision and pressure profile to enhance spinal support.

Other aspects of the invention include methods, devices, systems, components, improvements and other technology related to the concepts described in this document.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 3 is a table summarizing the features of each sleep state.

FIG. 4A is a top view of a mattress showing example divisions for pressure and temperature adjustment zones.

FIG. 6B illustrates a surface support system for providing support for body zones under prone, lateral and supine sleeping positions.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

I. Overview of Operation

The process of sleep can be divided into stages or states, such as Pre-sleep, Falling Asleep, Sleep, Waking Up, and a variety of possible night disruptions. Each of these stages benefits from a specific set of conditions. To determine what stage the user is in, an ISE may monitor the user's body position and biometric data, and combine this information with past trends. From there, the system matches the user's sleep state to appropriate mattress and environment settings.

A. Core Systems and Subsystems

Figure 1:
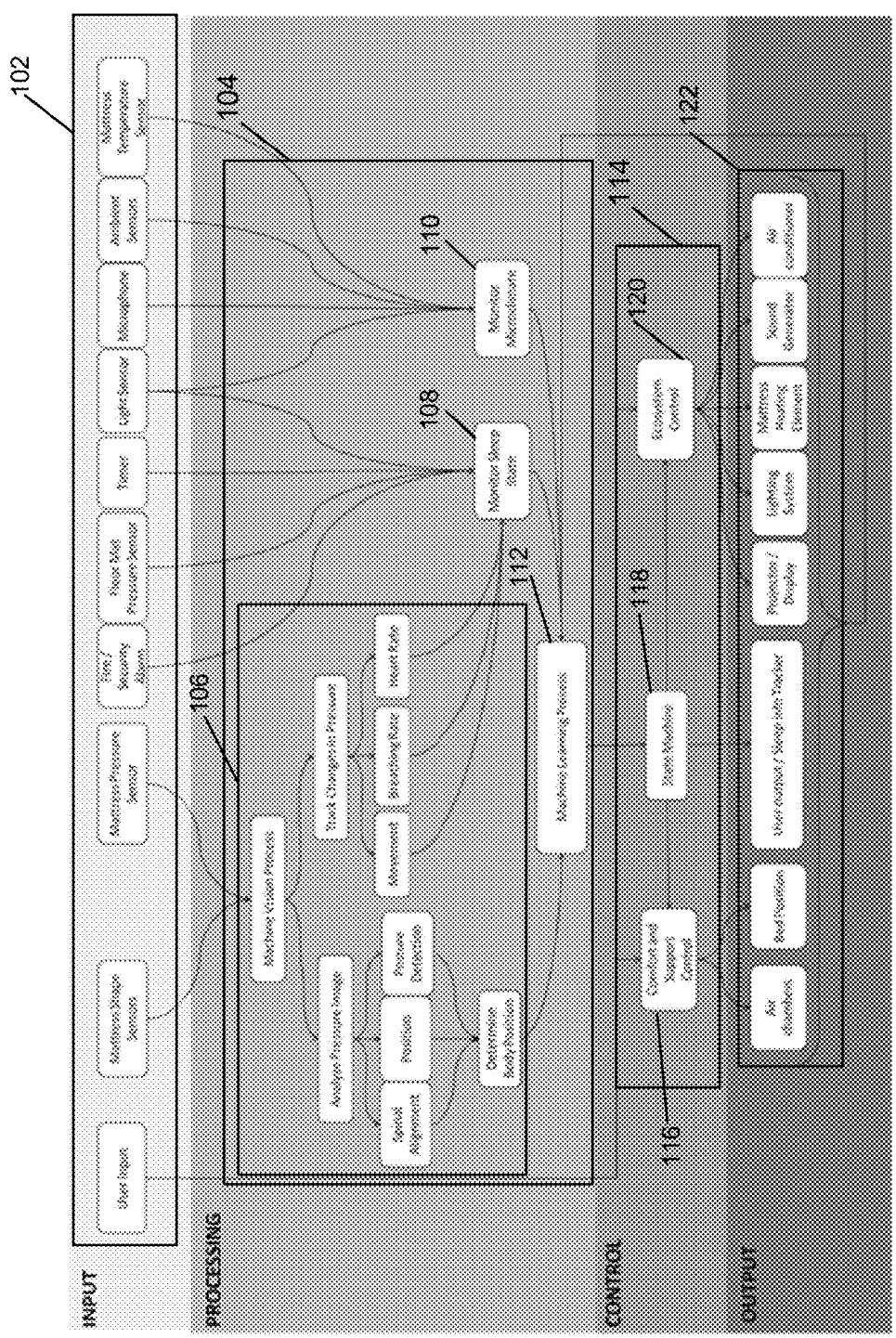
FIG. 1 is a diagram of the operation process of an example sleep ecosystem.

FIG. 1 is a diagram of a sleep ecosystem's operation process. The functions of this example ISE are divided into the following subsystems which monitor the conditions of the sleep environment, process this information to determine the necessary changes, and carry out these actions.

Sleep Monitoring System Inputs 102:

Integrated sensors monitor, for example, the mattress microclimate and ambient room temperature, light and noise levels, and receive user input settings.

Sleep Monitoring System Processing 104:

Inputs are processed to detect, for example, a user's posture and sleep state.

1. Pressure-sensing system 106: Pressure and indentation profiles, body position and posture, movement and other biological data such as heart rate are extracted from pressure images using machine vision.
2. Sleep Stage Monitoring System 108: Position, posture, movement, and vital signs are used to determine if the user is present, whether they are asleep, and how deeply.
3. Sleep Environment Monitoring System 110: Ambient room temperature, sleep surface temperature, light and noise levels, and other sleep environment conditions are processed and monitored.
4. Machine Learning Process 112: The current sleep stage, mattress and environment conditions are compared and correlated with past trends to improve sleep state detection and refine the settings associated with each state.

Sleep Environment Control System 114:

Sleep environment is adjusted based on, for example, the user's posture and sleep state.

1. State Machine 118: The user's sleep stage, the time of night and previous activity are taken into consideration and the system transitions to the most appropriate state.
2. Comfort and Support Control System 116: The mattress contour adjusts according to the user's posture and system state to relieve body pressure, provide proper spinal alignment, and promote either sleep or wakefulness.
3. Ecosystem Control System 120: According to the system state, air-conditioning, sound and light modules react to adjust the ambient environment.

B. Sleep State Control and State Machine

Figure 2:
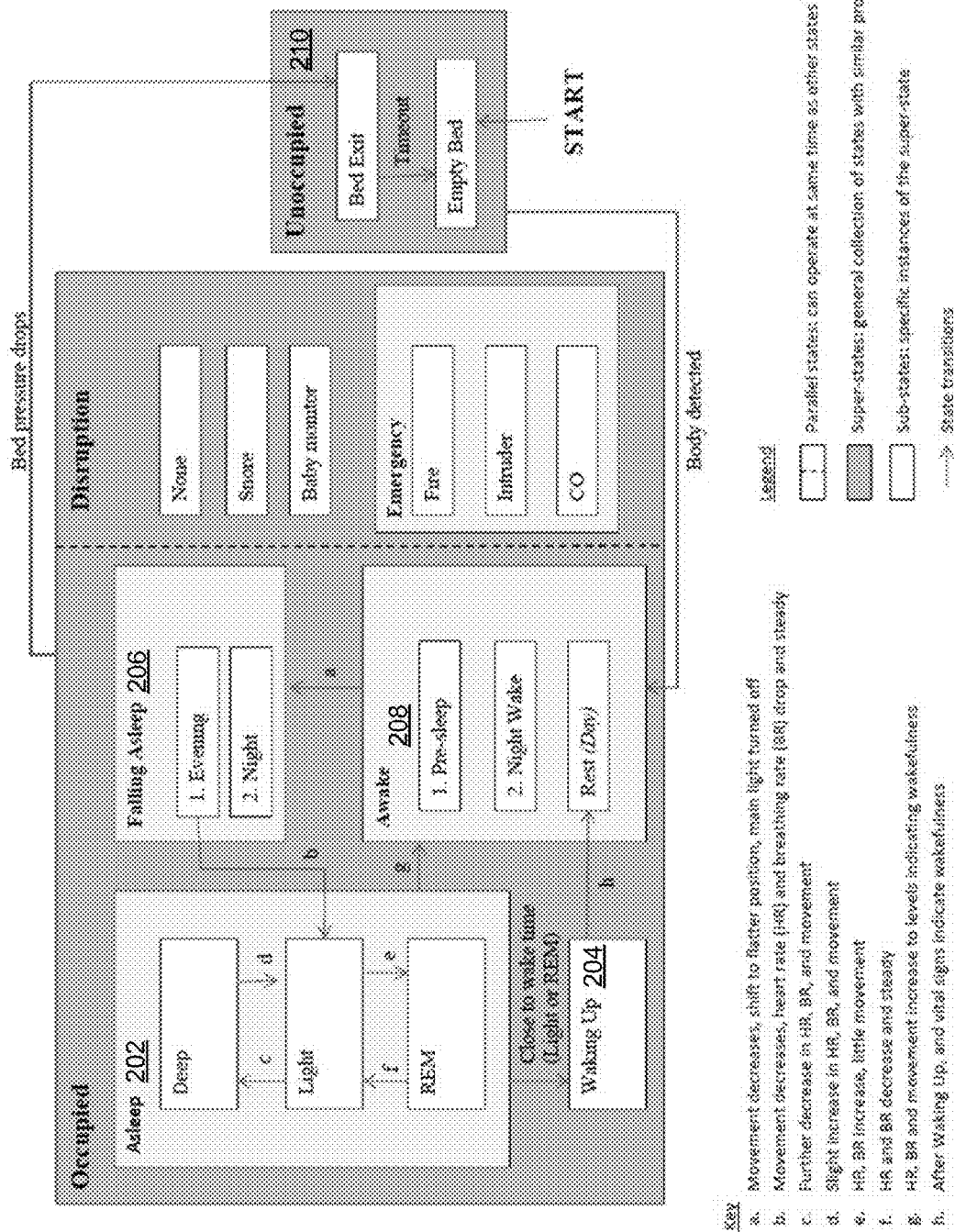
FIG. 2 is an example state machine diagram for an ISE.

The ISE functions by transitioning amongst states which each correspond to a point or condition during the sleep cycle. A trigger, such as a body movement, signals to the system that a change has occurred and that it should shift to a state which best suits this change. The ISE features a manual mode, where the settings and transitions between each state are initiated by the user, or an automatic mode which learns and adapts to the user over time. To simplify the operation, the ISE is organized into hierarchal states: broad conditions containing more specialized instances. One example organization of these states and a summary of their features are shown in FIG. 2.

When a person enters the bed, the system transitions to the Awake 208 state and a specific sub-state (e.g., Pre-sleep, Night Wake, or Rest) depending on the time of day. From there, the system responds to the user's progression through sleep. If the user awakens at any time during the night, the system shifts to the Night Wake state, and transitions to Unoccupied 210 whenever the user leaves the bed, then back to Falling Asleep 206 (Night). If an emergency arises, the ISE will wake the user by vibrating the mattress, lights and alarms. It also softly rouses the user to respond to a baby monitor, or roll a sleeper on to their side to mitigate snoring. When it is close to the time for the user to wake up, the bed will begin its Waking Up 204 program and afterwards the user may remain in bed in the Rest state under Awake 208, or leave the bed. Main features of the key states are summarized in FIG. 3.

II. Ecosystem Features: Sleep Support System

The sleep support system (e.g., a mattress) is one element of the ISE. In this example, it includes integrated pressure and temperature sensors, a contour layer of adjustable, inflatable air chambers, and an overlying comfort layer. The mattress is divided into zones, such as in FIG. 4A, to provide the correct firmness and temperature for each region of the body. For example, a layer 401 of air chambers can be divided into body zones: head 402, torso 403, and leg 404. Temperature zones 406 through 408 correspond to head, torso, and leg, respectively.

Figure 4B:
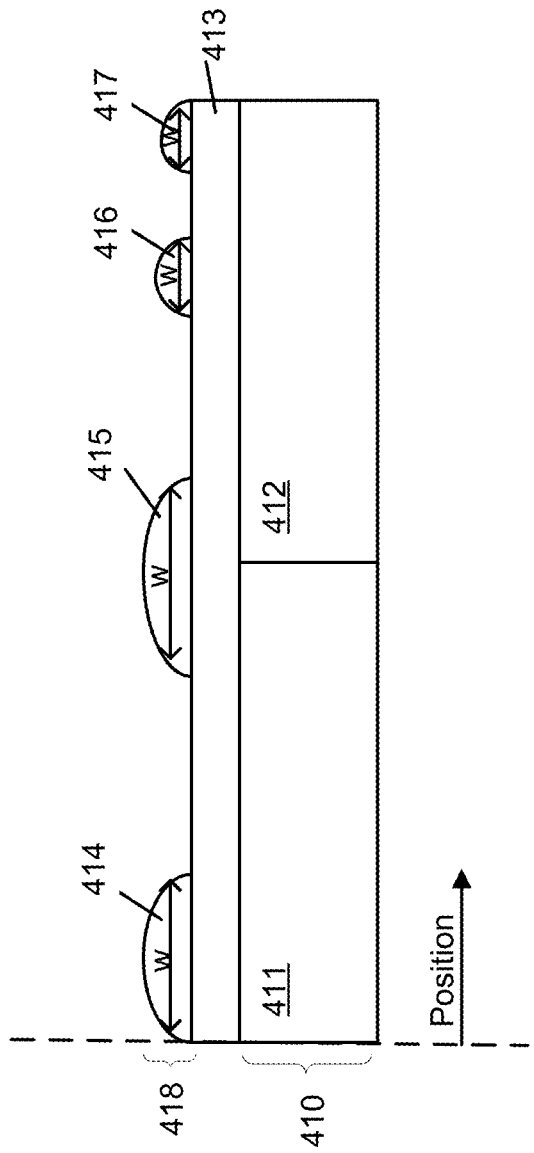
FIG. 4B illustrates a surface support system of an example mattress.

The mattress may include a surface support system for adjusting the mattress surface to conform to the user's sleep position, as shown in FIG. 4B. The illustrated mattress 420 includes a core support layer 410, a comfort layer 413, and a surface support layer 418. The core support layer 410 includes an upper body zone 411 and a lower body zone 412. The comfort layer 413 includes pressure relief zones. The surface support layer 418 includes a head zone 418, a lumbar spine zone 415, a knee zone 416, and a calf/ankle zone 417 for heel relief. The surface support zones 414 through 417 each may adjust its relative position on the mattress 420 and width.

A. Detecting Posture

Figure 5:
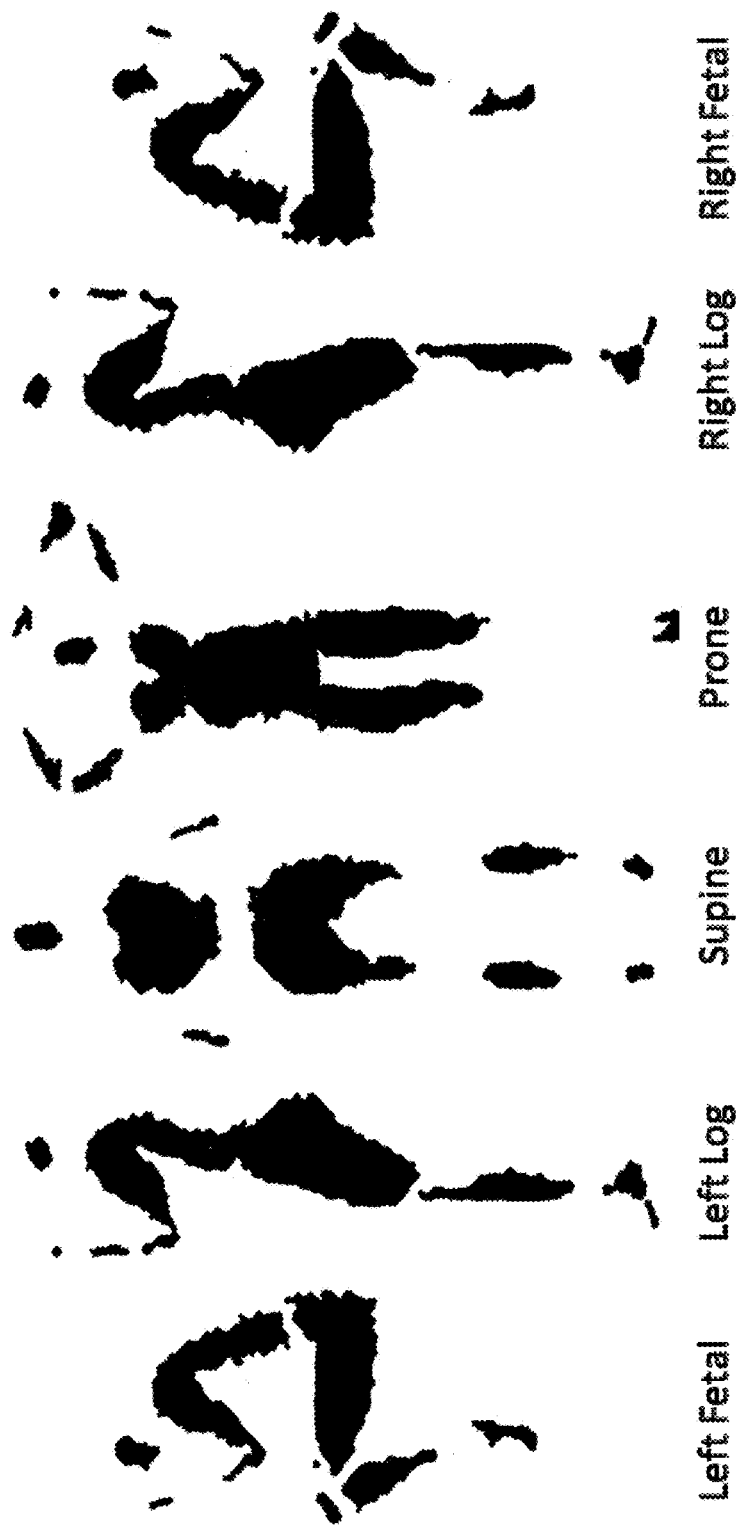
FIG. 5 shows representative pressure images for six main sleeping postures.

Detecting the user's posture on the mattress enables the system to provide correct pressure relief and spinal support. To classify the user's posture, machine vision is used to extract geometric features from pressure images, which are then compared to a database of example images and sorted into one of six main positions (e.g., Left Fetal, Left Log, Supine, Prone, Right Log, and Right Fetal) as illustrated in FIG. 5 or an intermediate.

Figures 12, 13:
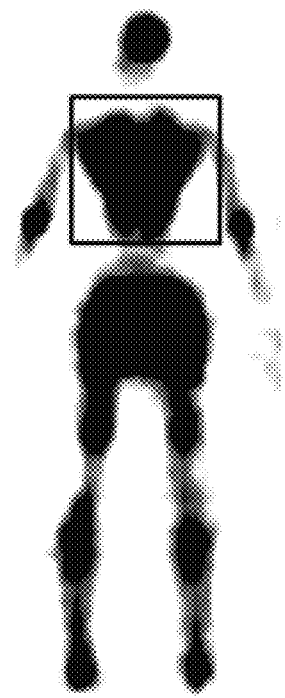
FIG. 12 is a table of pressure features used to classify sleep postures.
FIG. 13 is a machine vision image illustrating segmenting the thorax region.

Referring now to FIG. 12, sleeping postures can be classified based on the pressure features shown in FIG. 12. First, the pressure images are centered, smoothed and normalized. Geometrical features such as coverage (e.g., proportion of image covered, coverage of 25% of pressure, coverage of 50% of pressure, coverage of 75% of pressure, coverage over 8 fixed rectangular regions), symmetry (e.g., measure of pressure symmetry) and balance (e.g., measure of pressure on both sides of images), direction of curvature (e.g., measure of curvature of pressure image), hip features, and shoulder features are extracted from the pressure image. Finally, Minimum Class Residual Sparse Classification is used to compare the image to previously classified images (i.e., training data) to determine the most likely posture. The training data could be created by assigning a class to sample pressure images. First, these images would be centered and normalized to eliminate variations of location and body weight. Next, geometrical features such as hip position, symmetry, and direction of curvature would be extracted from the images, and stored as a column vector $a_{ij}$, where i is the class number and j represents the sample number within that class.

Combining n samples of m features into a matrix $A_{m\,n}$ creates a database to measure new samples against and assign them an appropriate class label. To classify a new sample y, sparse representation with $l_0$ minimization may be used, finding a vector x so that y=Ax, with the minimum number of non-zero elements. This produces a vector expressing the sample y as a weighted sum of training samples as shown in Equation (1):

$$y=a_{11}x_1+a_{12}x_2+\ldots+a_{ij}x_n \qquad (1),$$

where i is the number of class labels and j is the number of training samples for the i-th class. The non-zero elements of x correspond to the training samples which represent the new sample well. From there, the sample would be categorized by finding the class which minimizes the class residual, or the error between y and the sample reconstructed from x multiplied by a matrix of the representative class samples as shown in Equation (2):

$$i=\mathrm{argmin}_k\|y-A_{ir}x_n\| \qquad (2).$$

For example, if a person was sleeping in supine position, the system would extract pressure features from the pressure image, such as the relatively symmetrical distribution of pressure, and store them in a vector. By solving the system y=Ax, y can be represented as a linear combination of the most similar training samples. The vector x would be multiplied by matrices containing only the samples from the same class, a "prone" matrix, a "supine matrix" and the like. These reconstructed vectors would then be compared to the original sample by finding the distance between the sample spaces. Finally, the sample y is assigned the class corresponding to the reconstructed vector which gave the minimum residual. In this case, the "supine" matrix should contain the largest number of similar samples, and so the error between y and the vector reconstructed from samples of supine postures will be the smallest.

Secondly, the contour of the mattress is measured or estimated from the pressure profile to determine the shape of the user's spine. Tilt sensors integrated into the pressure sensor or additional indentation sensors are used to create an elevation profile of the mattress, and then to infer the sleeper's spinal alignment. Once the sleeper's spine shape is determined, it is compared to a reference shape, and the firmness of target zones may be iteratively adjusted until the estimated spine shape is within a threshold value of the reference shape. According to this information, the system then determines how to adjust the firmness of each zone and best support the user.

B. Adjusting the Mattress Contour

Actively conforming the mattress surface to the user's position improves sleep quality and leads to more refreshing rest. The core of the mattress includes independently controlled air chambers which inflate or deflate to equalize pressure and hold the spine in proper alignment. These chambers are organized into three main zones: head, torso and leg.

Figure 6A:
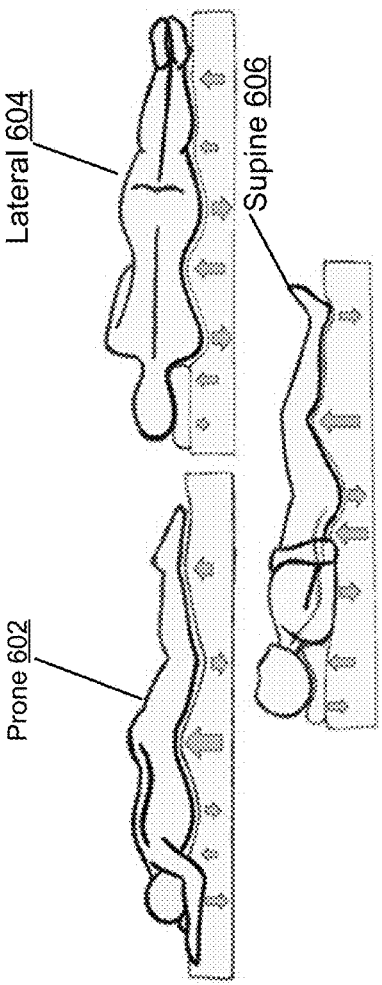
FIG. 6A is a table showing preferred support for prone, lateral and supine sleeping positions.

FIG. 6A is a table showing preferred support for prone, lateral and supine sleeping positions. The three main categories for positions are prone 602, lateral 604 and supine 606. Proper alignment is similar to standing with a flattened lumbar, and each position requires specific support. When a prone posture is detected, the mattress may lower the head area, increase firmness under the abdomen, and soften the knee area. For a lateral posture, the mattress may raise the head area until the neck is straight, and soften under the shoulders and hips, while supporting the sleeper's waist and elevating the ankles slightly above the pelvis. In a supine position, the area under the neck may raise to support a neutral neck position while keeping the head level, increase firmness under the lumbar and knees, and soften slightly under the shoulders, hips and heels. Finally, if the sleeper is detected to be in an intermediate position, the bed adjusts to minimize the pressure points, and compare the spine shape to the closest main posture. In one embodiment, these adjustments are implemented using inflatable air bladders (e.g., a layer 402 of air chambers illustrated in FIG. 4A). Alternate technologies include actuated mattress segments or pistons, different arrangements of air bladders and other fluid filled chambers.

In some embodiments, the mattress surface is adjusted to conform to the user's position which improves spine support and leads to a more refreshing rest. Specific support is provided for various body regions such as lumbar spine, head, knees, and heels. For different sleep positions, these body regions have different support requirements. As illustrated in FIG. 6B, a surface support system can be adjusted to provide support required by different body regions for different sleep positions. Adjustment of the surface support system is activated using the machine vision component of the ISE after a change in position has occurred.

Surface support bladders may be adjusted to rise up to contour key locations on the body, and the core support system is adjusted to provide support through immersion into the core support zones. Additional surface support bladders allow better fine tuning of spinal alignment that is not possible with core support bladders alone and thereby improving comfort.

In one embodiment, the surface support system is the top surface of the ISE. For example, multiple air bladders are located at the head zone, lumbar spine zone, knee zone, and calf/ankle zone. These surface support zones are customizable in position relative to one another, and width, to accommodate a range of body sizes. The surface support system includes a lower leg or calf/ankle zone reduces pressure in the heels region as the heels are one of the most common areas of discomfort when lying in the supine position. For medical applications, this is important for the reduction or prevention of pressure ulcers.

C. Monitoring Changes in Pressure

Additional information is gleaned from the pressure image by tracking the signal over time. The user's movement is used, as in actigraphy, to quantify measure restlessness and aid in sleep detection. Calculating the energy of movements over time has been shown an effective method to aid in determining a person's state of wakefulness. Additionally, the user's heart and respiration rate is tracked via subtle periodic oscillations of the user's center of mass, for example ballistocardiography (BCG). The pressure signal is filtered and processed to isolate body movement, heart rate and respiration rate.

Ballistocardiography (BCG) is a method for determining heart rate (HR) and breathing rate (BR) by measuring the oscillatory motions and changes in a sleeper's center of gravity caused by the action of the heart, and the motion of a person's thorax while breathing. The overall pressure intensity oscillates with this periodic motion, the pressure over time signal can be processed and filtered to obtain measurements as accurate as 0.4% for HR and 1.5% for BR. The following is an example process for Determining Breathing and Heart Rate:

1. Scan entire surface at 1 Hz

Figure 7:
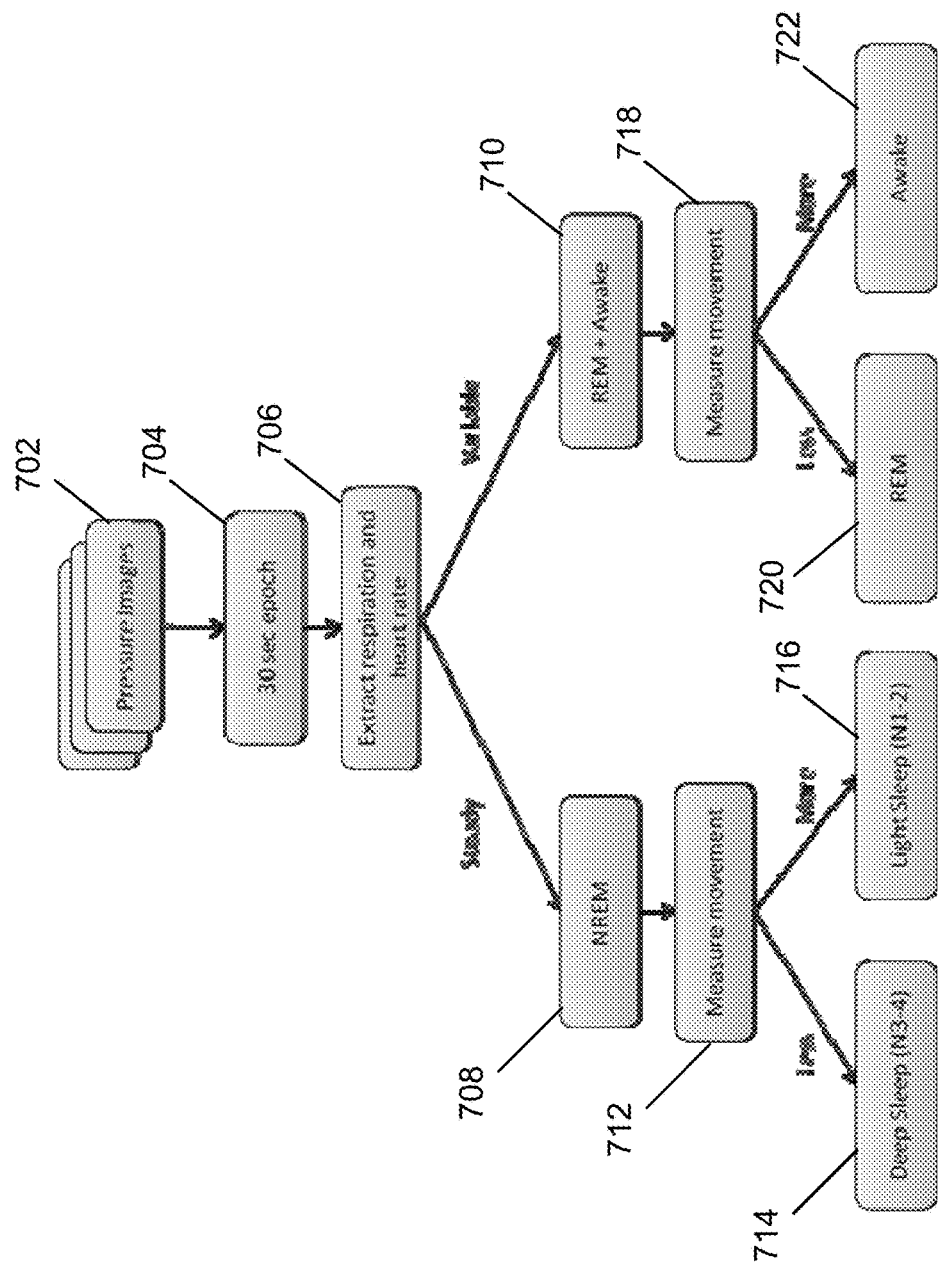
FIG. 7 is a decision tree showing the process of determining sleep states.
Figure 14:
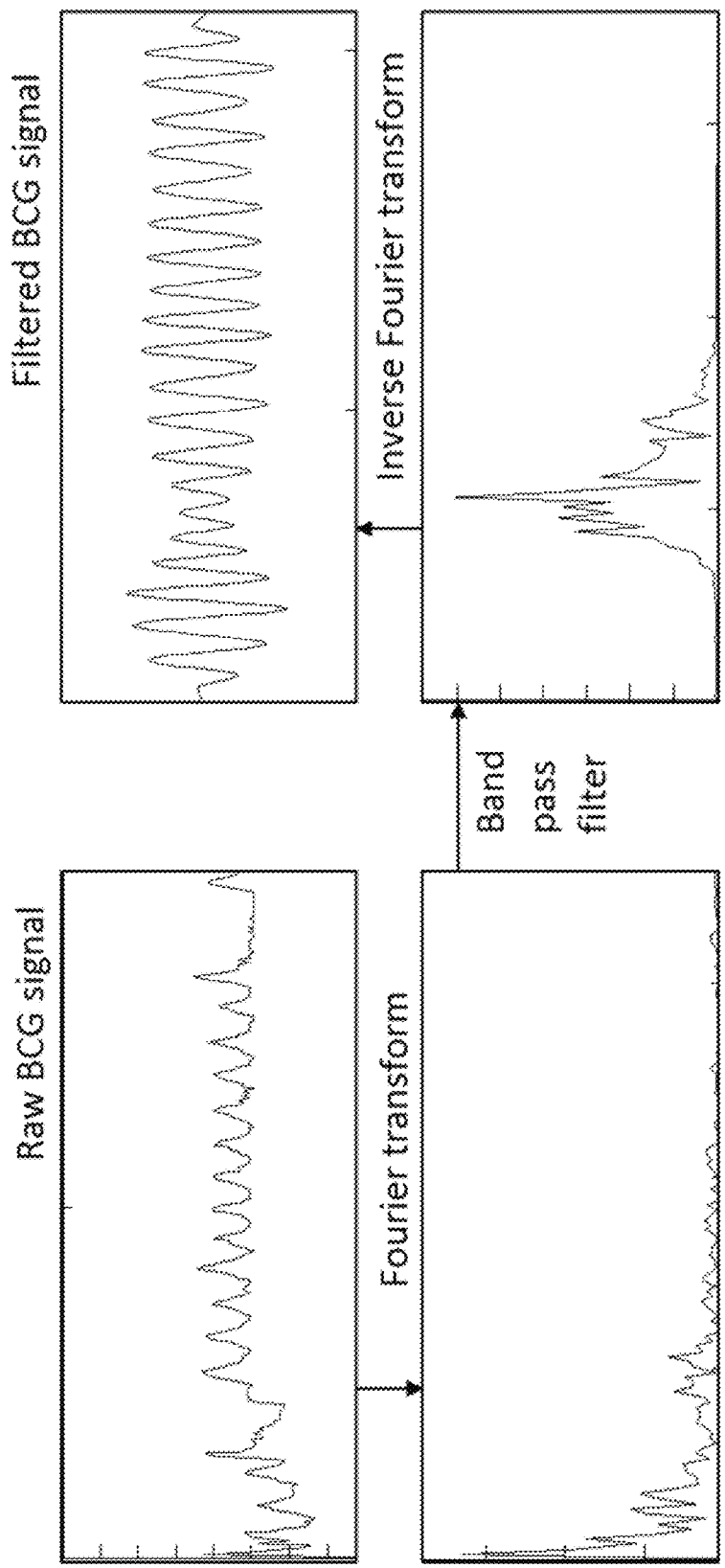
FIG. 14 illustrates a process for extracting heart rate (HR) and breathing rate (BR) from pressure data.

2. Use machine vision to identify the thorax region (see FIG. 13)
3. Oversample this area at 10+Hz
4. Track the motion of the thorax Center of Pressure (COP) along the length of body
5. Find calm periods in the signal by segmenting out movement artefacts, i.e. periods where the COP movement has higher than average energy
6. Run the calm signals through a band-pass filter (see FIG. 14):
   a. HR: 0.5-1.5 Hz (30-90 beats per minute)
   b. BR: 1/6-1/3 Hz (10-20 cycles per minute)
7. Find peaks in the signals and calculate time between each one (inter-beat interval, "IBI")
8. Calculate breaths or beats per minute D. Monitoring Sleep States Determining the user's sleep stage is important to the operation of the ISE. People move less as sleep deepens, and have slower, more regular heart and respiration rates. Using this information, the ISE classifies the user's sleep stage and logs the data for future reference, and for the user's own information. Once the system has determined the user's sleep stage, and therefore which state of operation it should enter, the comfort and environment control systems adjust the sleep ecosystem to produce the better conditions for the user at that point in time. FIG. 7 shows a process for classifying the user's sleep stage based on heart rate and movement. Pressure images are created 702 are divided 704 into thirty-second periods, as is standard practice in polysomnography and clinical sleep studies, and analyzed 706 for heart and respiration rates. From there, the user's movement during that period is analyzed and the sleep stage is determined. When the user's movement is steady 708, the user is in the non-rapid eye movement sleep (NREM) sleep stage. When the user's movement is variable 710, the user is in the rapid eye movement (REM) sleep stage. When a user is determined to be in the NREM sleep stage, the user's movement continues to be measured 712. Less movement indicates the user is in the deep sleep (N3-4) 714 stage and more movement indicates the user is in the light sleep (N1-2) stage 716. When a user is determined to be in the REM sleep stage, the user's movement continues to be measured 718. Less movement indicates the user remains in the REM 720 stage and more movement indicates the user is in the awake 722 stage. In an alternate approach, sleep state is determined based on polysomnography, EEG, or actigraphy using electrodes, head/wrist bands or remote sensing.

III. Ecosystem Features: Environment

The bed frame and headboard of the ISE houses modules for adjusting the mattress temperature and humidity, ambient light and sound, as well as manual controls and display features. Also, a pressure-sensitive bedside mat may be included to indicate the presence of anyone beside the bed.

A. Temperature and Humidity

Figure 8:
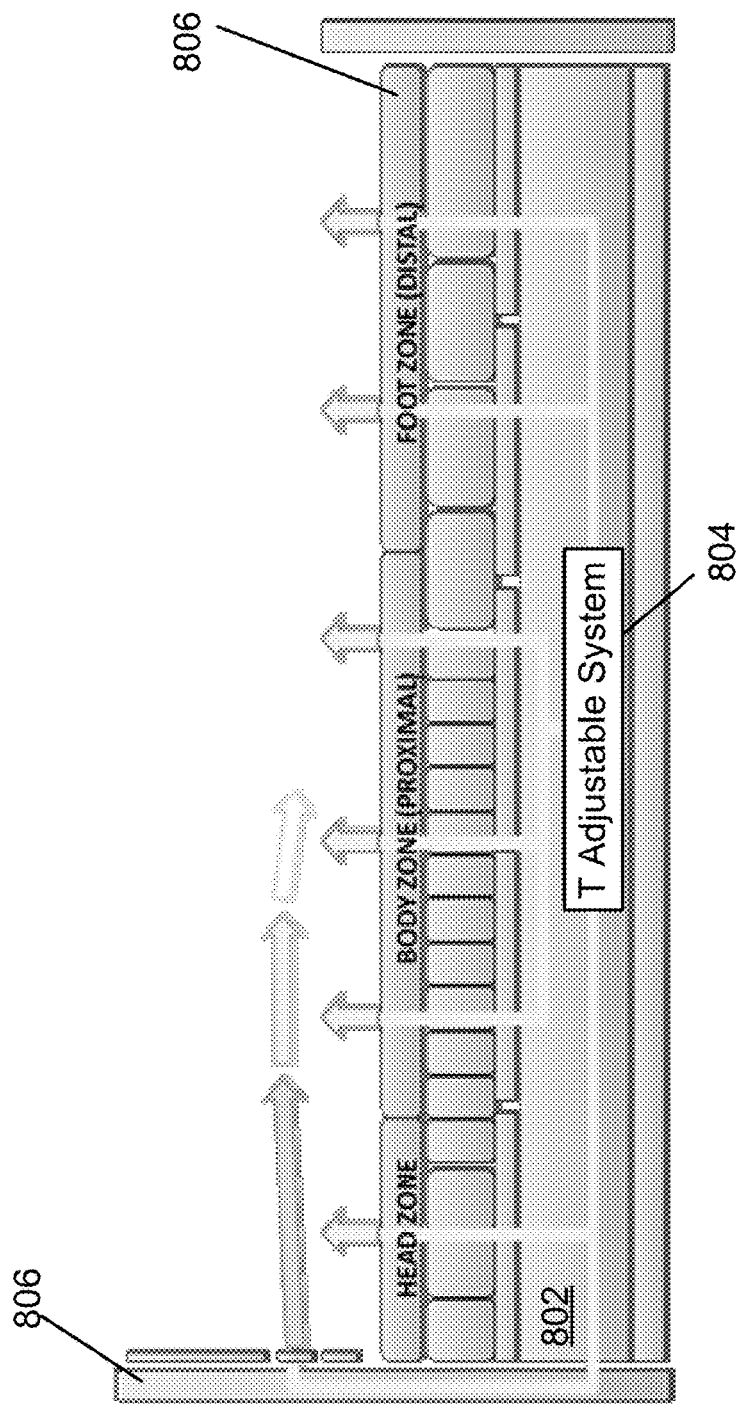
FIG. 8 is an illustration of an example air-flow system.

This system actively controls and monitors the temperature of head, body (or torso) and foot (or leg) zones in the mattress and the quality of air directly above the user. The system controls the temperature including bed surface temperature and ambient temperature according to temperature measurements such as bed surface temperature measurement and ambient temperature measurements, sleep state detection, and/or user settings. Temperature is closely linked to sleep quality and circadian rhythms. A warm bed in the evening and cool during the night induces deeper, more restful sleep. The system may determine an optimal temperature set point and control heating or cooling to maintain the optimal set point. FIG. 8 shows an example temperature adjustable system such as an air conditioning element 804 housed in the bed base 802 below the mattress 806, and vents in the mattress material and headboard allow the flow of conditioned air over the sleeper. Air circulates through vents in the mattress to six temperature zones—three for each occupant. A curtain of air over sleepers is provided though vents in the headboard 808. Alternatively, a temperature adjustable system such as an electric or water-based/fluid-based temperature control layer may be integrated into the mattress. Passive cooling materials such as gels and gel-infused foams may also be used. The mattress may also be divided into different temperature zones. The atmosphere is important for overall comfort and respiratory health, and so during the night, and so air flowing through the headboard vents is filtered to remove allergens and maintained at a humidity of 40-50%.

During the day, distal skin temperature is approximately 2° C. cooler than proximal skin near the core, and warming the body, especially the feet, before sleep decreases sleep onset latency and increases deep sleep. The optimal ambient temperature for sleep during the night is cool, approximately 16-19° C. Conversely, when waking up, cooling the extremities and warming the core can decrease "sleep inertia" and help people wake up more easily, increasing alertness. Following the connection between temperature and circadian rhythms, the mattress alters its temperature according to the occupant's sleep stage, as follows:

Getting into bed: all zones warm, keep skin temperature at 35° C.

Falling asleep: foot zone skin temperature 2° C. warmer than core

During the night: uniform cool temperature, keep skin at 34° C.

Waking up: core zone skin temperature 2° C. warmer than feet

To monitor the sleeper's skin temperature, the mattress could incorporate flexible temperature sensors called thermal ribbons, use temperature-sensing fabric in its construction, or measure the returning temperature of the heating fluid.

B. Light Regulation

This module regulates the colour and level of light the user is exposed to. Lights which simulate the sun's cycle have been used to aid sleep: warm light in the evening and bluer light in the morning help regulate the body's circadian rhythm and establish a regular sleep pattern.

The lighting features of the ISE include:

Dimmable LED panels in the headboard and frame for soft glowing light

Manual, preset or programmable settings for lighting throughout the night

Three settings for light colour
  3000K: warm light for the evening and night to prevent sleep disruptions
  4000K: neutral light for daytime and reading
  6000K: cool blue light to increase alertness in the morning A motion sensor on the bed base which turns on warm light if the occupant leaves during the night, and turns off when they return Dusk simulation:
  Bed senses the occupant is ready for sleep
    Decrease in motion
    Flatter posture
  Change light to 2700K and decrease from 200-0 lux over 30 minutes Dawn simulation:

Bed senses the occupant is ready to wake up
- Within ~45 minutes of wake time
- Sleeper in light sleep or REM
- Gradually increase from 0-200 lux of 6700K light Alternate lighting technologies include external lamps, overhead lighting fixtures and/or series of differently coloured light bulbs in headboard or bed frame.

In addition, to prevent the light of one user disturbing the other, the bed may be equipped with retractable awnings which extend from the headboard when a light is activated. If one user is asleep while the other is awake, the awning may open on the side of the light source, and retract once the light is switched off.

C. Sound Programs

Sound programs help mask environmental noise, and specific frequencies can be used to either induce and enhance sleep, or promote alertness. In this system, directional speakers embedded in the headboard or close to the user's head emit personally tailored sound programs according to their preference and detected sleep state. The module includes a variety of sound programs for different effects, such pink, white or grey noise, or nature sounds. The user can operate the sound module manually, or set it to automatic, in which the system selects the best types, times, and volumes of sound according to recorded sleep data and the present ambient noise level.

Pink noise, which is sound with energy inversely proportional to the frequency, at 60 dB significantly decreases sleep latency and induces more deep sleep. It is believed that brain waves may synchronize with the low frequencies in this sound, and so induced greater amounts of deep sleep when compared to quiet nights.

Binaural beats are structured stereo sounds which have a beat frequency which can be set to oscillate at rates observed in the brainwaves associated with different stages of sleep. They influence states of awareness by synchronizing large regions of the brain, helping to promote and maintain sleep or wakefulness. Frequencies less than 4 Hz promote the Delta waves found in deep sleep, and frequencies of 7-14 Hz promote alpha waves present in wakeful relaxation.

During the night, the ISE matches sound features to the user's sleep state as follows:

Falling asleep: begin sleep-inducing sounds e.g. pink noise and binaural beats matched to the slowing of brainwaves During the night: adjust volume to environmental noise level Waking up: switch to awareness-increasing sounds e.g. alpha-wave simulating sounds when dawn simulation commences Alternate technologies could include external sound machine and noise screens, speakers in a headband or pillow, vibration mechanism in the mattress and/or environmental noise-cancelling system.

D. Connectivity

Users expect devices to interface seamlessly with each other, and providing Wi-Fi capability and connectivity gives the ISE yet another level of convenience. The ISE may have the following functions:

Respond to a variety of commands, either manual, motion or voice

Be Wi-Fi enabled to communicate and interface with other smart devices

Figure 9:
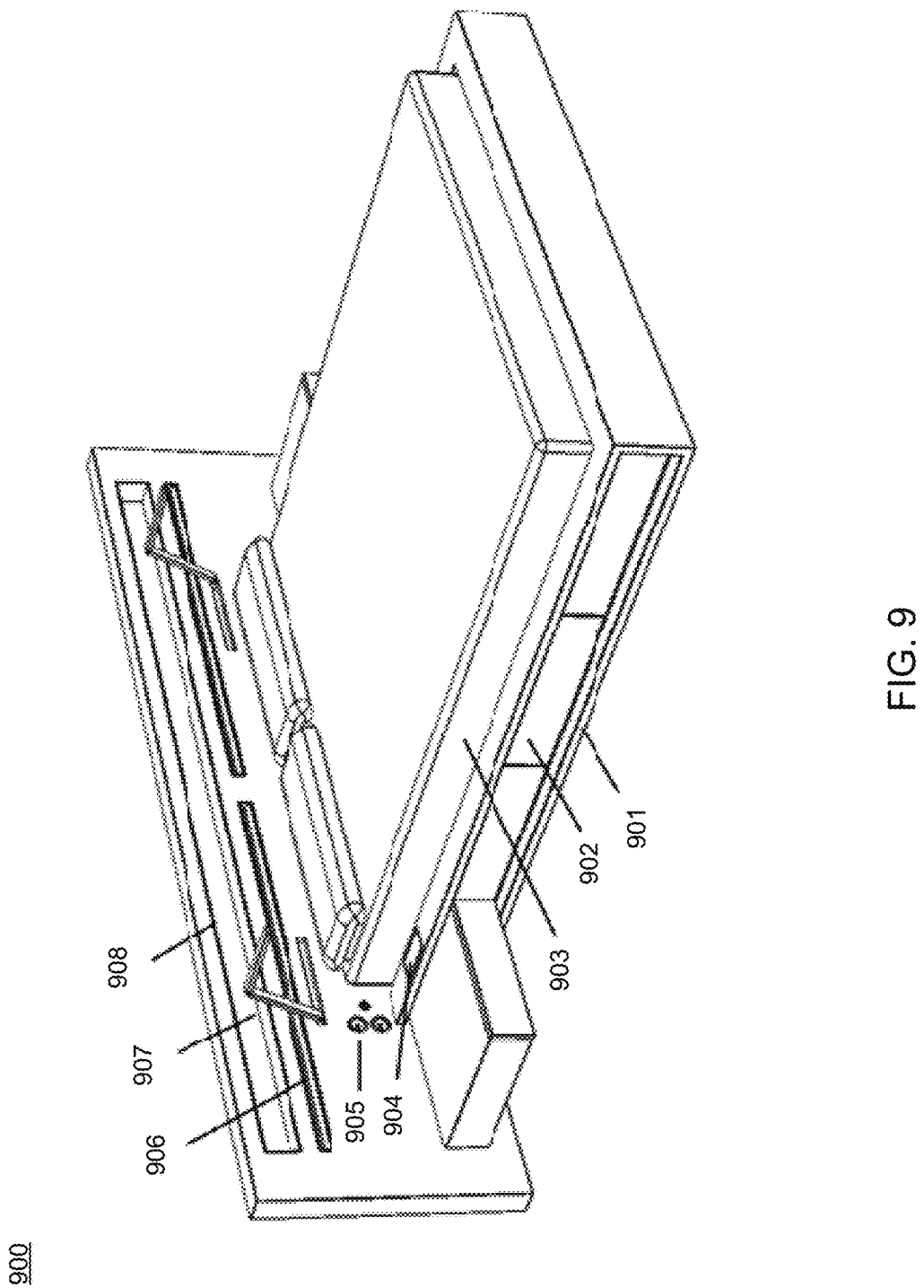
FIG. 9 is a perspective view of an ISE.
Figure 10:
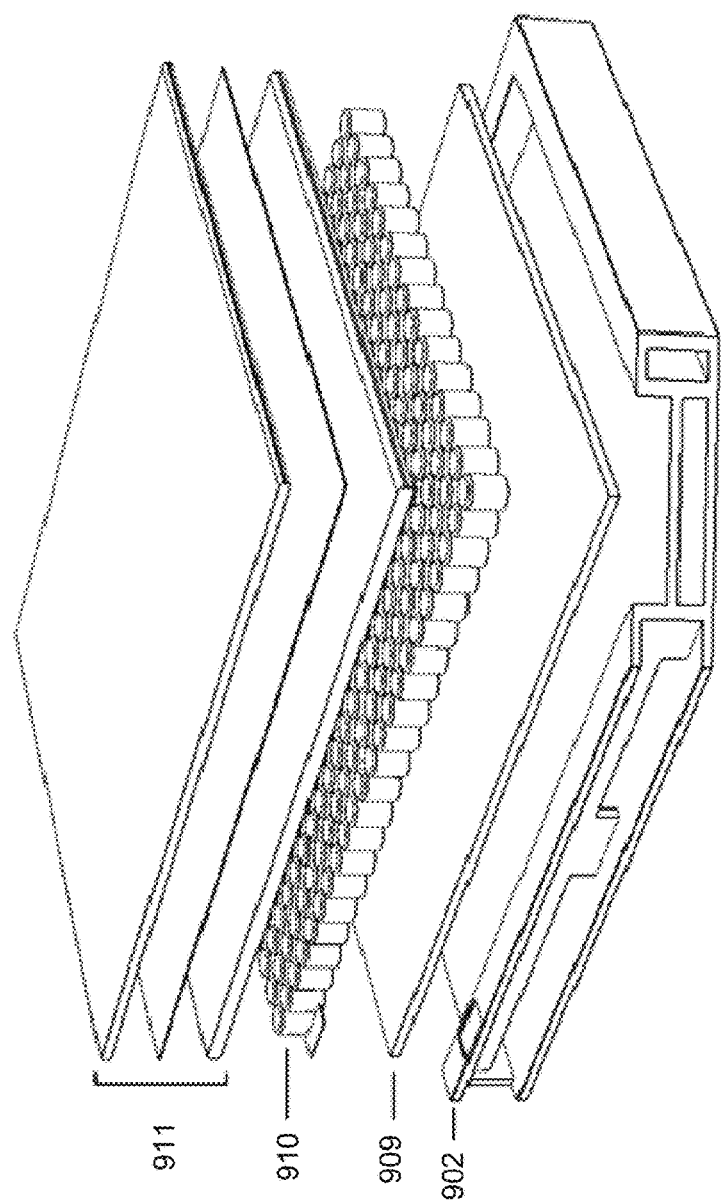
FIG. 10 is an exploded view showing layers of the ISE.
Figure 11:
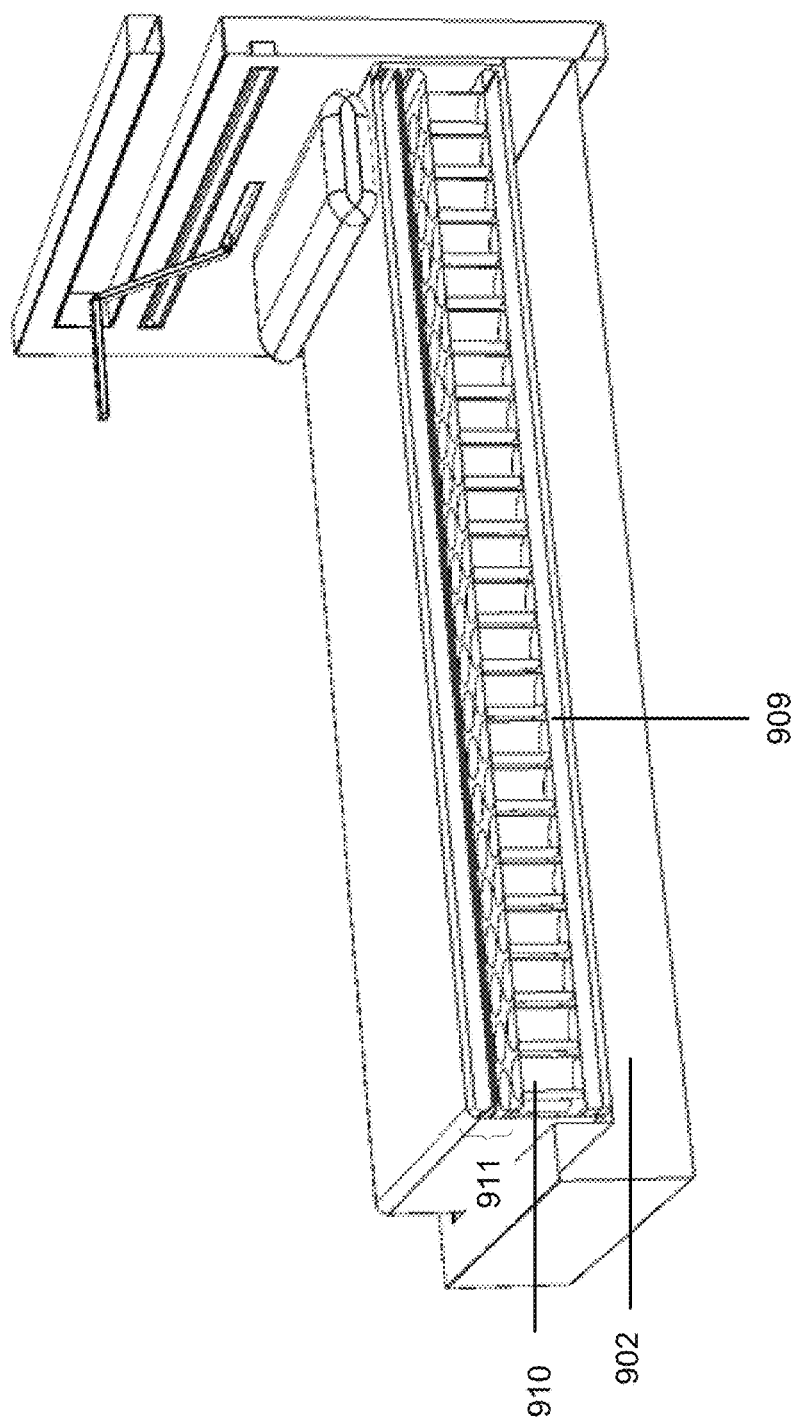
FIG. 11 is a cutaway view of the ISE.

Connect to an app which controls the bed, tracks sleep data and saves preferences Interface with the house's security system to alert of intruders, fires or other emergencies Be equipped with a projector to display the time, weather, the days tasks and/or the news on the ceiling, wall, or screen upon awakening IV. ISE Structure FIGS. 9-11 are different views of an example ISE 900. Mechanical and electrical components are housed below the mattress in the bed frame of the ISE, while the inflatable air bladders, pressure and temperature sensors are integrated into the mattress structure. Light and sound generating components are located in the headboard and bedside tables, along with controls and other auxiliary features such as light screens and adjustable reading lamps. The numbered features are described below.

Floor lights 901: illuminate the floor for middle of the night bed exits.

Bed base 902: houses electrical and mechanical components: air pressure regulators, air conditioning and filtering unit, and control and processing components.

Mattress 903: made up of layers including an adjustable base, air chambers, pressure sensor, temperature regulating layer, comfort layer and mattress topper.

Bedside controls 904: buttons or touchpad to manual control the ISE, and connect mobile devices Speakers 905: embedded, directional speakers near the user's head emit focused, personalized sound to block unwanted noise and enhance sleep or wakefulness.

Air vent 906: in the headboard blows a curtain of filtered, humidified and heated or cooled air over the user.

Reading lamp 907: a moveable lamp to provide directed light and not disturb the other occupant.

Light panel 908: glowing LED panels in the headboard provide soft light for evening and mornings.

Adjustable bed base 909: actuated segments below the mattress control the overall contour of the mattress, allowing the user to sit upright, raise their legs, etc.

Air bladders 910: chambers divided into sections inflate or deflate to change the mattress contour Additional layers 911: a pressure sensor, temperature sensing and regulating layer, comfort layer and/or mattress topper complete the mattress structure.

i. Pressure Sensor: high-resolution sensors track the pressure and movement of the users ii. Temperature zones: the surface of the mattress is divided into zones and air vents, water or electric heating/cooling devices deliver specific temperature control to targeted body sections.

iii. Comfort layer: latex, foam or springs covering air bladders for comfort and pressure relief. Pressure and indentation sensors may be incorporated into this layer.

iv. Mattress topper: a quilted layer of wool, cotton or another material for comfort, aesthetics and moisture wicking. Temperature sensors may be embedded in this layer.

In alternate embodiments, aspects of the invention are implemented in computer hardware, firmware, software, and/or combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

What is claimed is:

1. A sleep ecosystem comprising:
   an adjustable sleep support system comprising a sleep surface to support a sleeper during sleep;
   a sleep monitoring system including pressure sensors integrated with the adjustable sleep support system to measure surface pressure values of the sleeper on the sleep surface and configured to detect a posture and a sleep state of the sleeper supported by the sleep surface by:
      using machine vision techniques to process the measured surface pressure values to determine a location of the sleeper's thorax,
      processing time variations in the measured surface pressure values in an area of the thorax to determine periodic oscillations of the sleeper's thorax,
      determining a heart rate and/or a respiration rate of the sleeper from the determined periodic oscillations, and
      determining the sleep state based on the determined heart rate and/or respiration rate; and
   a sleep environment control system coupled to the sleep support system and the sleep monitoring system, and configured to adjust the sleep support system according to the posture and the sleep state of the sleeper.

2. The sleep ecosystem of claim 1, wherein the sleep monitoring system is further configured to detect at least one of a body movement, a heart rate or a respiration rate, and is further configured to determine the sleep state based on the detected body movement, heart rate and/or respiration rate.

3. The sleep ecosystem of claim 1, wherein the sleep state is selected from a group of sleep states include falling asleep, asleep, and waking up.

4. The sleep ecosystem of claim 3, wherein the group of sleep states further includes deep asleep, light asleep and REM asleep.

5. The sleep ecosystem of claim 1, wherein the sleep monitoring system includes temperature sensors integrated with the sleep support system to measure surface temperature values of the sleep surface; and the sleep environment control system adjusts a temperature of the sleep support system according to the measured surface temperature values and to a user temperature setting.

6. The sleep ecosystem of claim 5, wherein the sleep environment control system adjusts the temperature of the sleep support system further according to the sleep state of the sleeper.

7. The sleep ecosystem of claim 5, wherein the sleep support system is divided into different temperature zones, and the sleep environment control system adjusts a temperature of each temperature zone according to a body zone of the sleeper corresponding to that temperature zone.

8. The sleep ecosystem of claim 5, wherein the sleep environment control system includes an air-conditioning system integrated with the sleep support system and configured to provide a curtain of air over the sleeper.

9. The sleep ecosystem of claim 5, wherein the sleep environment control system further adjusts an ambient temperature according to the measured surface temperature values and user settings.

10. The sleep ecosystem of claim 1, wherein the sleep support system comprises a surface support system to adjust a shape of the sleep surface, and the sleep environment control system is further configured to adjust the surface support system such that the sleep surface conforms to the sleeper's posture.

11. The sleep ecosystem of claim 1, wherein the sleep monitoring system is further configured to use machine learning to refine future detections of the sleep state of the sleeper by analyzing the sleeper's past sleep state history.

12. The sleep ecosystem of claim 1, wherein the sleep monitoring system is configured to detect a shape of the sleeper's spine, and the sleep environment control system is further configured to adjust the sleep support system according to the shape of the sleeper's spine.

13. The sleep ecosystem of claim 12, wherein the sleep monitoring system further comprises indentation sensors to measure tilt values of the sleep surface, and the sleep monitoring system determines a spinal alignment of the sleeper based on the tilt values and a reference shape, and the sleep environment control system is further configured to adjust the sleep support system according to the spinal alignment.

14. The sleep ecosystem of claim 1, wherein the sleep environment control system adjusts the sleep support system separately for different body zones within the sleep support system, wherein different body zones correspond to different body regions of the sleeper.

15. The sleep ecosystem of claim 1, wherein the sleep support system comprises a mattress that is adjustable in overall contour.

16. The sleep ecosystem of claim 1, wherein the sleep support system comprises air chambers, and the sleep environment control system adjusts pressure values among the air chambers according to the posture of the sleeper.

17. The sleep ecosystem of claim 1, wherein the sleep environment control system is further configured to adjust at least one of humidity, an ambient light color, an ambient light level, a sound level, and a sound frequency for a sleep environment for the sleeper.

18. A sleep ecosystem comprising:
   an adjustable sleep support system comprising a sleep surface to support a sleeper during sleep, the adjustable sleep support system divided into different temperature zones;
   a sleep monitoring system including temperature sensors integrated with the sleep support system to measure surface temperature values of the sleep surface and configured to detect a posture and a sleep state of the sleeper supported by the sleep surface; and a sleep environment control system coupled to the sleep support system and the sleep monitoring system, and configured to adjust a sleep environment for the sleeper based on the posture and the sleep state of the sleeper and to adjust a temperature of the sleep support system according to the measured surface temperature values and to a user temperature setting, wherein the sleep environment control system adjusts a temperature of each temperature zone according to a body zone of the sleeper corresponding to that temperature zone.

19. The sleep ecosystem of claim 18, wherein the sleeping monitoring system comprises a state machine that detects the sleep state of the sleeper, and the state machine determines state transitions based on the sleep state, a time, and the sleeper's activities.

20. A method of providing the sleep ecosystem of claim 18 to the sleeper, comprising:

measuring, by the sleep ecosystem, surface pressure values of the sleep surface;

detecting and monitoring, by the sleep ecosystem, the sleep state of the sleeper according to the surface pressure values;

determining, by the sleep ecosystem, a sleep environment setting suitable for the sleeper based on the sleep state, and adjusting, by the sleep ecosystem, the sleep environment for the sleeper according to the sleep environment setting.

21. The sleep ecosystem of claim 18, wherein the sleep environment control system is further configured to adjust at least one of humidity, an ambient light color, an ambient light level, a sound level, and a sound frequency for a sleep environment for the sleeper.

22. The sleep ecosystem of claim 18, wherein the sleep support system comprises a mattress that is adjustable in overall contour.

23. The sleep ecosystem of claim 18, wherein the sleep state is selected from a group of sleep states include falling asleep, asleep, and waking up.

* * * * *